United States Patent
Hulot (10) Patent No.: US 12,351,634 B2
(45) Date of Patent: Jul. 8, 2025

(54) USE OF CILENGITIDE FOR AMELIORATING CARDIAC FIBROSIS OCCURRING IN RESPONSE TO MYOCARDIAL INFARCTION

(71) Applicants: INSERM (Institut National de la Santé et de la Recherche Médicale), Paris (FR); Université Paris Cité, Paris (FR); Assistance Publique-Hôpitaux de Paris (APHP), Paris (FR)

(72) Inventor: Jean-Sébastien Hulot, Paris (FR)

(73) Assignees: INSERM (INSTITUT NATIONAL DE LA SANTÉ ET DE LA RECHERCHE MÉDICALE), Paris (FR); UNIVERSITÉ PARIS CITÉ, Paris (FR); ASSISTANCE PUBLIQUE-HÔPITAUX DE PARIS (APHP), Paris (FR)

( * ) Notice: Subject to any disclaimer, the term of this patent is extended or adjusted under 35 U.S.C. 154(b) by 881 days.

(21) Appl. No.: 17/282,599

(22) PCT Filed: Oct. 9, 2018

(86) PCT No.: PCT/IB2018/001394
§ 371 (c)(1),
(2) Date: Apr. 2, 2021

(87) PCT Pub. No.: WO2020/074937
PCT Pub. Date: Apr. 16, 2020

(65) Prior Publication Data
US 2021/0347898 A1 Nov. 11, 2021

(51) Int. Cl.
*A61P 9/00* (2006.01)
*A61K 38/07* (2006.01)
*C07K 16/28* (2006.01)

(52) U.S. Cl.
CPC .......... *C07K 16/2848* (2013.01); *A61K 38/07* (2013.01); *A61P 9/00* (2018.01)

(58) Field of Classification Search
CPC .................................. A61P 9/00; A61K 38/00
See application file for complete search history.

(56) References Cited

U.S. PATENT DOCUMENTS

2010/0249396 A1* 9/2010 Suzuki ..................... A61P 35/04
540/523
2016/0264566 A1* 9/2016 DeGrado ............. C07D 417/12

FOREIGN PATENT DOCUMENTS

| WO | WO2016046225 | * | 3/2016 | ........... C07D 471/04 |
| WO | WO2016046226 | * | 3/2016 | ........... C07D 471/04 |
| WO | 2017/088974 A2 | | 6/2017 | |
| WO | 2017/088974 A3 | | 6/2017 | |

OTHER PUBLICATIONS

Mas-Murano et al. Cilengitide: the first anti-angiogenic small molecule drug candidate. Design, synthesis and clinical evaluation. Anti-Cancer Agents in Med. Chem., 10, 753-768, 2010. (Year: 2010).*
Creemers et al. Molecular mechanisms that control interstitial fibrosis in the pressure-overloaded heart. Cardiovasc. Res. 89, 265-272, 2011. (Year: 2011).*
www.medchemexpress/cilengitide. accessed Oct. 8, 2024. (Year: 2013).*
Sarrazy et al.; "Integrins αvβ5 and αvβ3 promote latent TGF-β1 activation by human cardiac fibroblast contraction"; Cardiovascular Research, vol. 102, No. 3, Mar. 17, 2014, pp. 407-417.
Murray et al.; "αv integrins on mesenchymal cells regulate skeletal and cardiac muscle fibrosis"; Nature Communications, vol. 8, No. 1, Oct. 24, 2017, entire article.
Bagnato et al.; "Dual αvβ3 and αvβ5 blockade attenuates fibrotic and vascular alterations in a murine model of systemic sclerosis"; Clinical Science, vol. 132, No. 2, Dec. 13, 2017, pp. 231-242.
Yasuda et al.; "T3 peptide, a fragment of tumstatin, stimulates proliferation and migration of cardiac fibroblasts through activation of Akt signaling pathway"; Naunyn-Schmiedeberg's Archives of Pharmacology, vol. 390, No. 11, Aug. 7, 2017, pp. 1135-1144.

* cited by examiner

*Primary Examiner* — Elly-Gerald Stoica
(74) *Attorney, Agent, or Firm* — WCF IP (57) ABSTRACT

Activated cardiac fibroblasts are essential for the production of extracellular matrix proteins that accumulate during cardiac fibrosis, and PW1+ cardiac adult stem cells were recently proposed as a cellular source of fibroblasts in the ischemic hearts. Here the inventors identify αV-integrin (or CD51) as an essential regulator of PW1+ cardiac adult stem cells fibrogenic behavior. Inhibition of αV-integrin reduce the profibrotic gene expression profile and the ability to differentiate into fibroblasts of cardiac PW1+ cells. The pharmacological blockade of αV-containing integrins improved cardiac function and survival after MI by reducing infarct size and attenuating the extension of reactive cardiac fibrosis. Notably, the total cardiac fibrotic area as well as interstitial fibrosis in the remote myocardial area are significantly reduced after pharmacological blockade of αV-containing integrins. These data identify a new mechanism that regulates cardiac fibrosis in response to an ischemic injury and suggest that pharmacological targeting of αV-integrin may provide clinical benefit in the treatment of cardiac fibrosis.

7 Claims, 4 Drawing Sheets

Specification includes a Sequence Listing.

SEQUENCE LISTING

```
<160> NUMBER OF SEQ ID NOS: 1

<210> SEQ ID NO 1
<211> LENGTH: 1048
<212> TYPE: PRT
<213> ORGANISM: Homo sapiens

<400> SEQUENCE: 1

Met Ala Phe Pro Pro Arg Arg Arg Leu Arg Leu Gly Pro Arg Gly Leu
1               5                   10                  15

Pro Leu Leu Leu Ser Gly Leu Leu Leu Pro Leu Cys Arg Ala Phe Asn
            20                  25                  30

Leu Asp Val Asp Ser Pro Ala Glu Tyr Ser Gly Pro Glu Gly Ser Tyr
        35                  40                  45

Phe Gly Phe Ala Val Asp Phe Phe Val Pro Ser Ala Ser Ser Arg Met
    50                  55                  60

Phe Leu Leu Val Gly Ala Pro Lys Ala Asn Thr Thr Gln Pro Gly Ile
65                  70                  75                  80

Val Glu Gly Gly Gln Val Leu Lys Cys Asp Trp Ser Ser Thr Arg Arg
                85                  90                  95

Cys Gln Pro Ile Glu Phe Asp Ala Thr Gly Asn Arg Asp Tyr Ala Lys
            100                 105                 110

Asp Asp Pro Leu Glu Phe Lys Ser His Gln Trp Phe Gly Ala Ser Val
        115                 120                 125
```

-continued

```
Arg Ser Lys Gln Asp Lys Ile Leu Ala Cys Ala Pro Leu Tyr His Trp
    130                 135                 140
Arg Thr Glu Met Lys Gln Glu Arg Glu Pro Val Gly Thr Cys Phe Leu
145                 150                 155                 160
Gln Asp Gly Thr Lys Thr Val Glu Tyr Ala Pro Cys Arg Ser Gln Asp
                    165                 170                 175
Ile Asp Ala Asp Gly Gln Gly Phe Cys Gln Gly Gly Phe Ser Ile Asp
                180                 185                 190
Phe Thr Lys Ala Asp Arg Val Leu Leu Gly Gly Pro Gly Ser Phe Tyr
                195                 200                 205
Trp Gln Gly Gln Leu Ile Ser Asp Gln Val Ala Glu Ile Val Ser Lys
    210                 215                 220
Tyr Asp Pro Asn Val Tyr Ser Ile Lys Tyr Asn Asn Gln Leu Ala Thr
225                 230                 235                 240
Arg Thr Ala Gln Ala Ile Phe Asp Asp Ser Tyr Leu Gly Tyr Ser Val
                    245                 250                 255
Ala Val Gly Asp Phe Asn Gly Asp Gly Ile Asp Asp Phe Val Ser Gly
                260                 265                 270
Val Pro Arg Ala Ala Arg Thr Leu Gly Met Val Tyr Ile Tyr Asp Gly
                275                 280                 285
Lys Asn Met Ser Ser Leu Tyr Asn Phe Thr Gly Glu Gln Met Ala Ala
    290                 295                 300
Tyr Phe Gly Phe Ser Val Ala Ala Thr Asp Ile Asn Gly Asp Asp Tyr
305                 310                 315                 320
Ala Asp Val Phe Ile Gly Ala Pro Leu Phe Met Asp Arg Gly Ser Asp
                    325                 330                 335
Gly Lys Leu Gln Glu Val Gly Gln Val Ser Val Ser Leu Gln Arg Ala
                340                 345                 350
Ser Gly Asp Phe Gln Thr Thr Lys Leu Asn Gly Phe Glu Val Phe Ala
                355                 360                 365
Arg Phe Gly Ser Ala Ile Ala Pro Leu Gly Asp Leu Asp Gln Asp Gly
    370                 375                 380
Phe Asn Asp Ile Ala Ile Ala Ala Pro Tyr Gly Gly Glu Asp Lys Lys
385                 390                 395                 400
Gly Ile Val Tyr Ile Phe Asn Gly Arg Ser Thr Gly Leu Asn Ala Val
                    405                 410                 415
Pro Ser Gln Ile Leu Glu Gly Gln Trp Ala Ala Arg Ser Met Pro Pro
                420                 425                 430
Ser Phe Gly Tyr Ser Met Lys Gly Ala Thr Asp Ile Asp Lys Asn Gly
                435                 440                 445
Tyr Pro Asp Leu Ile Val Gly Ala Phe Gly Val Asp Arg Ala Ile Leu
    450                 455                 460
Tyr Arg Ala Arg Pro Val Ile Thr Val Asn Ala Gly Leu Glu Val Tyr
465                 470                 475                 480
Pro Ser Ile Leu Asn Gln Asp Asn Lys Thr Cys Ser Leu Pro Gly Thr
                    485                 490                 495
Ala Leu Lys Val Ser Cys Phe Asn Val Arg Phe Cys Leu Lys Ala Asp
                500                 505                 510
Gly Lys Gly Val Leu Pro Arg Lys Leu Asn Phe Gln Val Glu Leu Leu
                515                 520                 525
Leu Asp Lys Leu Lys Gln Lys Gly Ala Ile Arg Arg Ala Leu Phe Leu
    530                 535                 540
Tyr Ser Arg Ser Pro Ser His Ser Lys Asn Met Thr Ile Ser Arg Gly
```

```
545                 550                 555                 560
Gly Leu Met Gln Cys Glu Glu Leu Ile Ala Tyr Leu Arg Asp Glu Ser
                565                 570                 575

Glu Phe Arg Asp Lys Leu Thr Pro Ile Thr Ile Phe Met Glu Tyr Arg
                580                 585                 590

Leu Asp Tyr Arg Thr Ala Ala Asp Thr Thr Gly Leu Gln Pro Ile Leu
                595                 600                 605

Asn Gln Phe Thr Pro Ala Asn Ile Ser Arg Gln Ala His Ile Leu Leu
            610                 615                 620

Asp Cys Gly Glu Asp Asn Val Cys Lys Pro Lys Leu Glu Val Ser Val
625                 630                 635                 640

Asp Ser Asp Gln Lys Lys Ile Tyr Ile Gly Asp Asp Asn Pro Leu Thr
                645                 650                 655

Leu Ile Val Lys Ala Gln Asn Gln Gly Glu Gly Ala Tyr Glu Ala Glu
                660                 665                 670

Leu Ile Val Ser Ile Pro Leu Gln Ala Asp Phe Ile Gly Val Val Arg
                675                 680                 685

Asn Asn Glu Ala Leu Ala Arg Leu Ser Cys Ala Phe Lys Thr Glu Asn
            690                 695                 700

Gln Thr Arg Gln Val Val Cys Asp Leu Gly Asn Pro Met Lys Ala Gly
705                 710                 715                 720

Thr Gln Leu Leu Ala Gly Leu Arg Phe Ser Val His Gln Gln Ser Glu
                725                 730                 735

Met Asp Thr Ser Val Lys Phe Asp Leu Gln Ile Gln Ser Ser Asn Leu
                740                 745                 750

Phe Asp Lys Val Ser Pro Val Val Ser His Lys Val Asp Leu Ala Val
                755                 760                 765

Leu Ala Ala Val Glu Ile Arg Gly Val Ser Ser Pro Asp His Val Phe
770                 775                 780

Leu Pro Ile Pro Asn Trp Glu His Lys Glu Asn Pro Glu Thr Glu Glu
785                 790                 795                 800

Asp Val Gly Pro Val Val Gln His Ile Tyr Glu Leu Arg Asn Asn Gly
                805                 810                 815

Pro Ser Ser Phe Ser Lys Ala Met Leu His Leu Gln Trp Pro Tyr Lys
                820                 825                 830

Tyr Asn Asn Asn Thr Leu Leu Tyr Ile Leu His Tyr Asp Ile Asp Gly
                835                 840                 845

Pro Met Asn Cys Thr Ser Asp Met Glu Ile Asn Pro Leu Arg Ile Lys
                850                 855                 860

Ile Ser Ser Leu Gln Thr Thr Glu Lys Asn Asp Thr Val Ala Gly Gln
865                 870                 875                 880

Gly Glu Arg Asp His Leu Ile Thr Lys Arg Asp Leu Ala Leu Ser Glu
                885                 890                 895

Gly Asp Ile His Thr Leu Gly Cys Gly Val Ala Gln Cys Leu Lys Ile
                900                 905                 910

Val Cys Gln Val Gly Arg Leu Asp Arg Gly Lys Ser Ala Ile Leu Tyr
                915                 920                 925

Val Lys Ser Leu Leu Trp Thr Glu Thr Phe Met Asn Lys Glu Asn Gln
                930                 935                 940

Asn His Ser Tyr Ser Leu Lys Ser Ser Ala Ser Phe Asn Val Ile Glu
945                 950                 955                 960

Phe Pro Tyr Lys Asn Leu Pro Ile Glu Asp Ile Thr Asn Ser Thr Leu
                965                 970                 975
```

```
Val Thr Thr Asn Val Thr Trp Gly Ile Gln Pro Ala Pro Met Pro Val
                980             985                 990
Pro Val Trp Val Ile Ile Leu Ala  Val Leu Ala Gly Leu  Leu Leu Leu
        995             1000                 1005
Ala Val Leu Val Phe Val Met  Tyr Arg Met Gly Phe  Phe Lys Arg
    1010                1015                1020
Val Arg Pro Pro Gln Glu Glu  Gln Glu Arg Glu Gln  Leu Gln Pro
    1025            1030                1035
His Glu Asn Gly Glu Gly Asn  Ser Glu Thr
    1040            1045
```

USE OF CILENGITIDE FOR AMELIORATING CARDIAC FIBROSIS OCCURRING IN RESPONSE TO MYOCARDIAL INFARCTION

FIELD OF THE INVENTION

The present invention relates to use of αV-integrin (CD51) inhibitors for the treatment of cardiac fibrosis.

BACKGROUND OF THE INVENTION

Heart failure (HF) remains a leading cause of mortality and hospitalizations worldwide and represents a heavy health care financial burden[1-6]. Current pharmacological treatments limit the peripheral consequences of cardiac dysfunction but there is a limited number of therapeutics that impact the primary adverse cardiac remodeling at the myocardial level. While the etiology of HF is diverse, HF is typically associated with a range of physiological and morphological changes including fibrosis of the myocardium[7-9]. Indeed, cardiac fibrosis is characterized by the excessive production and deposition of extracellular matrix (ECM) proteins into the myocardium which leads to normal tissue architecture disruption, reduced tissue compliance, mechanical and electrical dysfunction and which eventually accelerates the progression to HF[10,11]. However, as the mechanisms contributing to cardiac fibrosis are incompletely understood, there is currently no effective anti-fibrotic therapeutic strategy that could complement the current therapies for HF[9,11,12].

Activated cardiac fibroblasts are essential for the production of ECM proteins that accumulate during cardiac fibrosis, however, recent studies have established that cardiac fibroblasts represent a very heterogeneous cell population[10-14]. The exact nature of activated fibroblasts and consequently the sources of cardiac fibrosis remain poorly understood[9,12]. Different mechanisms have been reported including proliferation and activation of resident fibroblasts[15], transformation of endothelial and/or epicardial cells after injury through endothelial-mesenchymal transition and epithelial-mesenchymal transition respectively[16,17], migration of hematopoietic bone marrow-derived cells and perivascular cells[18]. Another model proposes that tissue resident progenitor populations activate in response to stress and become a major cellular source of organ fibrosis, including in the heart. In a recent study, we have identified a novel population of cardiac cells that reside in the myocardium and have a fibrogenic behavior in response to cardiac ischemic injury[19]. This population was identified based upon the expression of the pan-stem cell marker, Pw1/Peg3 (referred hereafter as PW1)[20,21], using a transgenic Pw1-beta galactosidase reporter mouse model. Taking advantage of the strong and produrant expression of the β-gal reporter enzyme, we found that a significant proportion (~22%) of fibroblasts were derived from PW1 expressing cells in ischemic hearts, therefore suggesting that cardiac PW1+ cells can contribute to cardiac fibrosis by directly giving rise to fibroblasts thus representing a source of additional ECM.

SUMMARY OF THE INVENTION

The present invention relates to use of αV-integrin (CD51) inhibitors for the treatment of cardiac fibrosis. In particular, the present invention is defined by the claims.

DETAILED DESCRIPTION OF THE INVENTION

Activated cardiac fibroblasts are essential for the production of extracellular matrix proteins that accumulate during cardiac fibrosis, and PW1+ cardiac adult stem cells were recently proposed as a cellular source of fibroblasts in the ischemic hearts. Here the inventors identify αV-integrin (or CD51) as an essential regulator of PW1+ cardiac adult stem cells fibrogenic behavior. Using a combination of transcriptomic and proteomic approaches, they identified the presence of αV-integrin in the plasma membrane of cardiac PW1+ cells. Expression analyses revealed αV-integrin expression as highly sensitive and specific to cardiac PW1+ cells. More than 93% of FACS-isolated cardiac PW1+ cells express CD51 and reciprocally more than 85% of PW1+ cells are recovered among the FACS-isolated CD51+ cardiac cells. Inhibition of αV-integrin reduce the profibrotic gene expression profile and the ability to differentiate into fibroblasts of cardiac PW1+ cells. Cardiac PW1+ cells showed a predominant expression of αVβ1 complex, a putative key mediator of organ fibrosis through TGF-beta activation. Consequently, pharmacological blockade of αV-containing integrins improved cardiac function and survival after MI by reducing infarct size and attenuating the extension of reactive cardiac fibrosis. Notably, the total cardiac fibrotic area as well as interstitial fibrosis in the remote myocardial area are significantly reduced after pharmacological blockade of αV-containing integrins. These data identify a new mechanism that regulates cardiac fibrosis in response to an ischemic injury and suggest that pharmacological targeting of αV-integrin may provide clinical benefit in the treatment of cardiac fibrosis.

Accordingly, the first object of the present invention relates to a method of treating cardiac fibrosis in a patient in need thereof comprising administering to the patient a therapeutically effective amount of a αV-integrin inhibitor.

As used herein, the term "cardiac fibrosis" has its general meaning in the art and refers to a condition characterized by the excessive production and deposition of extracellular matrix (ECM) proteins into the myocardium which leads to normal tissue architecture disruption, reduced tissue compliance, mechanical and electrical dysfunction. Cardiac fibrosis arises from aging, exposure to certain drugs, or in response to various heart diseases, such as myocardial infarction and hypertension. Following acute myocardial infarction, sudden loss of a large number of cardiomyocytes triggers an inflammatory reaction, ultimately leading to replacement of dead myocardium with a collagen-based scar. Several other pathophysiologic conditions induce more insidious interstitial and perivascular deposition of collagen, in the absence of completed infarction. Aging is associated with progressive fibrosis that may contribute to the development of diastolic heart failure in elderly patients. Pressure overload, induced by hypertension or aortic stenosis, results in extensive cardiac fibrosis that is initially associated with increased stiffness and diastolic dysfunction. Volume overload due to valvular regurgitant lesions may also result in cardiac fibrosis. Hypertrophic cardiomyopathy and post-viral dilated cardiomyopathy are also often associated with the development of significant cardiac fibrosis. Moreover, a variety of toxic insults (such as alcohol or anthracyclines) and metabolic disturbances (such as diabetes and obesity) induce cardiac fibrosis.

In particular, the αV-integrin inhibitor of the present invention is particularly suitable for limiting the development of reactive interstitial fibrosis in the viable myocardium. More particularly, the αV-integrin inhibitor of the present invention is suitable for improving cardiac function in a subject suffering from cardiac fibrosis. As used herein, the term "cardiac function" refers to the function of the heart, including global and regional functions of the heart. The term "global" cardiac function as used herein refers to function of the heart as a whole. Such function can be measured by, for example, stroke volume, ejection fraction, cardiac output, cardiac contractility, etc. The term "regional cardiac function" refers to the function of a portion or region of the heart. Such regional function can be measured, for example, by wall thickening, wall motion, myocardial mass, segmental shortening, ventricular remodeling, new muscle formation, the percentage of cardiac cell proliferation and programmed cell death, angiogenesis and the size of fibrous and infarct tissue. More particularly, the αV-integrin inhibitor of the present invention is suitable for improving survival of a subject suffering from cardiac fibrosis.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "αV-integrin" or "CD51" has its general meaning in the art and refers to that protein that in humans is encoded by the ITGAV gene. An exemplary human amino acid sequence of CD51 is represented by SEQ ID NO; 1. Integrins are heterodimeric integral membrane proteins composed of an alpha chain and a beta chain. αV undergoes post-translational cleavage to yield disulfide-linked heavy and light chains, that combine with multiple integrin beta chains to form different integrins. Among the known associating beta chains (beta chains 1,3,5,6, and 8; 'ITGB1', 'ITGB3', 'ITGB5', 'ITGB6', and 'ITGB8'), each can interact with extracellular matrix ligands.

```
>sp|P06756|ITAV_HUMAN Integrin alpha-V OS =
Homo sapiens OX = 9606 GN = ITGAV PE = 1 SV = 2
                                           SEQ ID NO: 1
MAFPPRRRLRLGPRGLPLLLSGLLLPLCRAFNLDVDSPAEYSGPEGSYFG

FAVDFFVPSASSRMFLLVGAPKANTTQPGIVEGGQVLKCDWSSTRRCQPI

EFDATGNRDYAKDDPLEFKSHQWFGASVRSKQDKILACAPLYHWRTEMKQ

EREPVGTCFLQDGTKTVEYAPCRSQDIDADGQGFCQGGFSIDFTKADRVL

LGGPGSFYWQGQLISDQVAEIVSKYDPNVYSIKYNNQLATRTAQAIFDDS

YLGYSVAVGDFNGDGIDDFVSGVPRAARTLGMVYIYDGKNMSSLYNFTGE

QMAAYFGFSVAATDINGDDYADVFIGAPLFMDRGSDGKLQEVGQVSVSLQ

RASGDFQTTKLNGFEVFARFGSAIAPLGDLDQDGFNDIAIAAPYGGEDKK

GIVYIFNGRSTGLNAVPSQILEGQWAARSMPPSFGYSMKGATDIDKNGYP

DLIVGAFGVDRAILYRARPVITVNAGLEVYPSILNQDNKTCSLPGTALKV

SCFNVRFCLKADGKGVLPRKLNFQVELLLDKLKQKGAIRRALFLYSRSPS

HSKNMTISRGGLMQCEELIAYLRDESEFRDKLTPITIFMEYRLDYRTAAD

TTGLQPILNQFTPANISRQAHILLDCGEDNVCKPKLEVSVDSDQKKIYIG

DDNPLTLIVKAQNQGEGAYEAELIVSIPLQADFIGVVRNNEALARLSCAF

KTENQTRQVVCDLGNPMKAGTQLLAGLRFSVHQQSEMDTSVKFDLQIQSS

NLFDKVSPVVSHKVDLAVLAAVEIRGVSSPDHVFLPIPNWEHKENPETEE

DVGPVVQHIYELRNNGPSSFSKAMLHLQWPYKYNNNTLLYILHYDIDGPM

NCTSDMEINPLRIKISSLQTTEKNDTVAGQGERDHLITKRDLALSEGDIH

TLGCGVAQCLKIVCQVGRLDRGKSAILYVKSLLWTETFMNKENQNHSYSL

KSSASFNVIEFPYKNLPIEDITNSTLVTTNVTWGIQPAPMPVPVWVIILA

VLAGLLLLAVLVFVMYRMGFFKRVRPPQEEQEREQLQPHENGEGNSET
```

As used herein the "αV-integrin inhibitor" refers to refers to any compound natural or not which is capable of inhibiting the activity or expression of αV-integrin. The term encompasses any antagonist that is currently known in the art or that will be identified in the future, and includes any chemical entity that, upon administration to a patient, results in inhibition or down-regulation of a biological activity associated with αV-integrin. The inhibitor can thus inhibit the expression or activity of αV-integrin, modulate or block the αV-integrin signalling pathway and/or block the binding of αV-integrin to a binding partner. The term also encompasses inhibitor of expression.

A significant number of αV-integrin antagonists (Goodman et al, Trends in Pharmacological Sciences, 2012, 33, 405; Tucker, Gordon C. "Alpha v integrin inhibitors and cancer therapy." Current opinion in investigational drugs (London, England: 2000) 4.6 (2003): 722-731; Hatley, Richard J D, et al. "An αv-RGD Integrin Inhibitor Toolbox: Drug Discovery Insight, Challenges and Opportunities." Angewandte Chemie International Edition 57.13 (2018): 3298-3321.) have been disclosed in the literature including inhibitory antibodies, peptides and small molecules.

In some embodiments, the αV-integrin inhibitor of the present invention is an antibody, more particularly an antibody having specificity for αV-integrin.

As used herein, the term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/11161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments. In some embodiments, the antibody of the present invention is a single chain antibody. As used herein the term "single domain antibody" has its general meaning in the art and refers to the single heavy chain variable domain of antibodies of the type that can be found in Camelid mammals which are naturally devoid of light chains. Such single domain antibody are also "Nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388.

In some embodiments, the antibody is a humanized antibody. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference.

In some embodiments, the antibody is a fully human antibody. Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference.

In some embodiments, the antibody of the present invention is a single chain antibody. As used herein the term "single domain antibody" has its general meaning in the art and refers to the single heavy chain variable domain of antibodies of the type that can be found in Camelid mammals which are naturally devoid of light chains. Such single domain antibody are also "Nanobody®".

In some embodiments, the antibody comprises human heavy chain constant regions sequences but will not induce antibody dependent cellular cytotoxicity (ADCC). In some embodiments, the antibody of the present invention does not comprise an Fc domain capable of substantially binding to a FcgRIIIA (CD16) polypeptide. In some embodiments, the antibody of the present invention lacks an Fc domain (e.g. lacks a CH2 and/or CH3 domain) or comprises an Fc domain of IgG2 or IgG4 isotype. In some embodiments, the antibody of the present invention consists of or comprises a Fab, Fab', Fab'-SH, F (ab')2, Fv, a diabody, single-chain antibody fragment, or a multispecific antibody comprising multiple different antibody fragments. In some embodiments, the antibody of the present invention is not linked to a toxic moiety. In some embodiments, one or more amino acids selected from amino acid residues can be replaced with a different amino acid residue such that the antibody has altered C2q binding and/or reduced or abolished complement dependent cytotoxicity (CDC). This approach is described in further detail in U.S. Pat. No. 6,194,551 by Idusogie et al.

Antibodies having specificity for αV-integrin are well known in the art and typically include intetumumab and abituzumab. Intetumumab is a pan alpha-v human monoclonal antibody that recognizes alpha-v beta-1, alpha-v beta-3, alpha-v beta-5, and alpha-v beta-6 integrins. Intetumumab competitively binds to and blocks both alpha-v beta-3 and alpha-v beta-5 integrins Abituzumab is a humanized monoclonal IgG2 antibody that specifically targets all αv integrins (Mitjans F, et al. J Cell Sci 1995; 108:2825-38; Monnier Y, et al. Cancer Res 2008:68; 7323-31).

In some embodiments, the αV-integrin inhibitor is Cilengitide. Cilengitide is a cyclic peptide antagonist that inhibits both αvβ1, αvβ3 and αvβ5. The IUPAC name of Cilengitide is 2-[(2S,5R,8S,11S)-5-benzyl-11-{3-[(diaminomethylidene)amino]propyl}-7-methyl-3,6,9,12,15-pentaoxo-8-(propan-2-yl)-1,4,7,10,13-pentaazacyclopentadecan-2-yl] acetic acid.

In some embodiments, the αV-integrin inhibitor is an inhibitor of αV-integrin expression respectively. An "inhibitor of expression" refers to a natural or synthetic compound that has a biological effect to inhibit the expression of a gene. In a preferred embodiment of the invention, said inhibitor of gene expression is a siRNA, an antisense oligonucleotide or a ribozyme. For example, anti-sense oligonucleotides, including anti-sense RNA molecules and anti-sense DNA molecules, would act to directly block the translation of αV-integrin mRNA by binding thereto and thus preventing protein translation or increasing mRNA degradation, thus decreasing the level of αV-integrin, and thus activity, in a cell. For example, antisense oligonucleotides of at least about 15 bases and complementary to unique regions of the mRNA transcript sequence encoding αV-integrin can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Small inhibitory RNAs (siRNAs) can also function as inhibitors of expression for use in the present invention. αV-integrin gene expression can be reduced by contacting a patient or cell with a small double stranded RNA (dsRNA), or a vector or construct causing the production of a small double stranded RNA, such that αV-integrin gene expression is specifically inhibited (i.e.

RNA interference or RNAi). Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically cells expressing αV-integrin. Typically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art. In some embodiments, the inhibitor of expression is an endonuclease. The term "endonuclease" refers to enzymes that cleave the phosphodiester bond within a polynucleotide chain. Some, such as Deoxyribonuclease I, cut DNA relatively nonspecifically (without regard to sequence), while many, typically called restriction endonucleases or restriction enzymes, and cleave only at very specific nucleotide sequences. The mechanism behind endonuclease-based genome inactivating generally requires a first step of DNA single or double strand break, which can then trigger two distinct cellular mechanisms for DNA repair, which can be exploited for DNA inactivating: the errorprone nonhomologous end-joining (NHEJ) and the high-fidelity homology-directed repair (HDR). In a particular embodiment, the endonuclease is CRISPR-cas. As used herein, the term "CRISPR-cas" has its general meaning in the art and refers to clustered regularly interspaced short palindromic repeats associated which are the segments of prokaryotic DNA containing short repetitions of base sequences. In some embodiment, the endonuclease is CRISPR-cas9 which is from *Streptococcus pyogenes*. The CRISPR/Cas9 system has been described in U.S. Pat. No. 8,697,359 B1 and US 2014/0068797. In some embodiment, the endonuclease is CRISPR-Cpf1 which is the more recently characterized CRISPR from Provotella and Francisella 1 (Cpf1) in Zetsche et al. ("Cpf1 is a Single RNA-guided Endonuclease of a Class 2 CRISPR-Cas System (2015); Cell; 163, 1-13).

By a "therapeutically effective amount" is meant a sufficient amount of the active ingredient for treating or reducing the symptoms at reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination with the active ingredients; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Typically the active ingredient of the present invention (e.g. αV-integrin inhibitor) is combined with pharmaceutically acceptable excipients, and optionally sustained-release matrices, such as biodegradable polymers, to form pharmaceutical compositions. The term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. In the pharmaceutical compositions of the present invention, the active ingredients of the invention can be administered in a unit administration form, as a mixture with conventional pharmaceutical supports. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

The invention will be further illustrated by the following figures and examples. However, these examples and figures should not be interpreted in any way as limiting the scope of the present invention.

FIGURES

FIG. 1. Cilengitide reduces cardiac fibrosis and improves cardiac function after MI. (A) Experimental design. Mice were pre-treated for 7 days with cilengitide or vehicle (n=16 per groups) before surgery and complete LAD ligation as an MI model (defined as Day 0). The mice were then followed and treated with cilengitide or vehicle for seven additional days. Final non-invasive and invasive evaluations were performed 7 days after surgery. (B) Survival curves in cilengitide vs vehicle treated mice in the seven days after MI. *p<0.05, log-rank test. (C) Left ventricular ejection fractions in cilengitide vs vehicle treated mice immediately before surgery and 7 days later. p<0.01, p<0.0001. (D) Typical masson trichome staining in vehicle and cilengitide treated animals and quantification of infarct size between both groups, *p<0.001, n=4 animal per groups. (E) Typical picrosirius red staining in vehicle and cilengitide treated animals and quantification of interstitial fibrosis in remote areas between both groups, ****p<0.0001, n=4 animal per groups.

FIG. 2. Cilengitide reduces the profibrotic activation of cardiac PW1+ cells (A) Quantitative PCR evaluation of acta2, mmp2, tgfrb1 and colla1 expression in isolated cardiac PW1+ cells cultured in presence of escalating concentrations of cilengitide (0 for vehicle only, 300 nM, 1000 nM). Data are expressed as means±SEM (n=4 in duplicate). *p<0.05, p<0.01 and *p<0.001 for Kruskal-Wallis test between all groups; #p<0.05, ##p<0.01 for Dunn's comparison with vehicle treated cells. (B) Quantification of β-gal+ cells within the vimentin-positive cells in vehicle and cilengitide post-MI heart sections, n=30 fields from 3 animals per groups, *p<0.05. (C). Quantification of β-gal+ and vimentin-negative cells within the total number of cells in vehicle and cilengitide post-MI heart sections, n=30 fields from 3 animals per groups, ***p<0.001.

EXAMPLE

Methods:

All procedures and animal care were approved by our institutional research committee and conformed the animal care guideline in Directive 2010/63/EU European Parliament.

Myocardial Infarction by LAD Ligation

Male 8 weeks-old C57BL/6 or PW1-reporter (PW1$^{nLacZ}$) mice were anesthetized in an induction chamber with 2% isoflurane mixed with 1.0 L/min 100% 02 and placed on a supine position on a heating pad to maintain body temperature. The mice were intubated with endotracheal tube and then connected to a rodent ventilator (180 breaths/min and a tidal volume of 200 µl). During surgical procedure anesthesia is maintained at 1.5-2% isoflurane with $O_2$. The chest was accessed from the left side through the intercostal space and the pericardium incised. The left anterior descending coronary artery (LAD) was exposed and encircled with a 8.0 prolene suture at the apex of the left ventricle. The suture was briefly snared to confirm the ligation by blanching the arterial region. Mice were analyzed 7 days after LAD permanent ligation.

Male C57BL/6J mice (Janvier labs) or PW1-reporter (PW1$^{nLacZ}$) mice received Cilengitide at 10 mg/kg/day (Adooq bioscience, ref: A12372) or vehicle i.p. for 14 days. LAD surgery was performed 7 days after starting cilengitide or vehicle administration. Mice were divided in 4 groups: MI-CIL (Cilengitide), MI-Veh (vehicle), Ctrl-CIL and Ctrl-Veh. At Day 14, animals were euthanatized and hearts were carefully collected, incubated for 2 h at 4° C. in 4% Formaldehyde solution (Ted Pella) then 24 h in 30% sucrose/PBS solution before OCT embedding and frozen in liquid nitrogen vapours. Echocardiographic measurements were taken at days 0 and 7 to assess cardiac function.

Cell Isolation and Fluorescence-Activated Cell Sorting

Animals were injected with heparin (100 UI/25 g) before euthanasia. The right atrium was carefully nicked with surgical scissors and the heart was perfused with 10 mL of PBS (Gibco) through the right ventricle to remove the blood. After collecting the heart, the atria were trimmed away and the ventricles were finely sliced (0.5-1 mm$^3$). Cardiac cells were dissociated at 37° C. for 30 min by enzymatic digestion with 480 U/mL collagenase II (Worthington) in DPBS (GIBCO). The digestion was stopped with DMEM (Life Technologies) supplemented into 10% FBS (Sigma) and 1% penicillin/streptomycin (P/S; Life Technologies) and the cell suspension was filtered through 100 µm Falcon cell strainer before centrifugation at 416 g for 10 min at 4° C. The cell pellet was re-suspended in 500 µL of Red Blood Cell Lysing (RBCL) Buffer to lyse red blood cells at RT for 30 sec. DPBS was added before 10 min centrifugation in same conditions as above. The cell pellet was then re-suspended in 300 µL of HBSS (Gibco) containing 1% FBS (HBSS-1% FBS) to perform immunostaining for 45 min on ice in dark. The list of antibodies used is reported in supplemental table 1. After incubation, HBSS-1% FBS was added and cells centrifuged at 416 g for 10 min at 4° C. to perform PW1+ cells staining. For this, 300 µL of HBSS-1% FBS containing 60 µM of 5-Dodecanoylaminofluorescein Di-β-D-Galactopyranoside ($C_{12}$FDG, ThermoFisher Scientific) a substrate for β-gal detection by flow cytometry was added on cells then incubated in dark at 37° C. for 1 h under constant agitation. Reaction was stopped by the addition of HBSS-1% FBS. After cell centrifugation, the pellet was re-suspended in 200 µL of HBSS-1% FBS, the viability dye propidium iodide (Sigma) was added and the samples were filtered through a 50 µm Filcon (BD bioscience) just before the analysis.

Viability threshold was determined by comparing conditions with and without viability dye. All immunostained populations were obtained by comparing signals from unstained cells and Fluorescence minus one conditions. B-Gal activity threshold was obtained by comparing B-Gal negative and positive cells.

RNA-Seq 300 ng of total RNA extracted from freshly isolated cells were used to perform library preparation with SureSelect Strand-Specific RNA kit (Agilent), according to the manufacturer's instructions. The resulting library was quality checked and quantified by peak integration on Bioanalyzer High sensitivity DNA labchip (Agilent). A pool of equal quantity of 12 purified libraries was done, each library being tagged with a different index. miRNAs pool libraries were finally sequenced on Illumina Hiseq 1500 instrument using a rapid flowcell. The pool was loading on 2 lanes of the flowcell. A paired End sequencing of 2×100 bp was performed.

After discarding reads that did not pass the Illumina filters and trimming sequenced bases with low quality (q<28) using the Cutadapt program[24], we restricted our downstream analyses to reads with length greater than 90 bp. Selected reads were mapped to a murine reference transcriptome that was generated by the RSEM package[25] from the full mouse reference genome and the gtf transcript annotations file from ENSEMBL[26]. Alignment and estimation of transcripts abundance in each of the 12 processed samples were performed using the RSEM program. Transcripts with abundance counts higher than 10 in more than 2 samples (N=36,948) were considered as expressed and kept for further analysis. Abundances of transcripts assigned to the same gene were combined together leading to the profiling of 16,403 gene expressions. A principal component analysis was then performed on the 12 expression profiles and revealed that the first three principal components explained ~84% of the total variability of gene expression profiling. The percentage of variability explained by the first, second and third component were 39.4%, 28.5% and 15.7%, respectively. Analyses were conducted under the R environment (version 3.2.2).

A Galaxy 15.10 instance was locally installed on a server machine. WolfPsort, TMHMM, and SignalP were obtained from CBS prediction servers (http://www.cbs.dtu.dk/services/). As NetNEs was not implemented in Galaxy, NLStradamus and PredictNLS were used in replacement. Each population RNASeq was then processed through a pipeline designed to select sequences containing a signal peptide, at least 1 transmembrane segment, no nuclear export signal and a theoretical presence at the plasma membrane. Intentionally loose filters were chosen as putative membranome were manually quality checked for false positive sequences and compared to several databases (Qiagen's Ingenuity Pathway Analysis, Uniprot, Ensembl). Finally, all samples were compared and only sequences found only in PW1+ cells but insensible to myocardial infarction.

Proteomics $PW1^+$ FACS sorted cells samples were prepared for MS analysis with an adapted protocol as too few cells was recovered to perform the complete protocol. 300 000 $PW1^+$ sorted cells were centrifuged at 500 g for 10 min at 4° C. Pellet was lysed in 100 µL of lysis buffer (10 mM HEPES, 1.5 mM MgCl2, 10 mM KCl, 0.5 mM DTT, 1 mM orthovanadate and protein inhibitor cocktail) and incubated for 15 min on ice. A mechanical cell disruption was then performed with 20 up and downs with a dounce potter. Samples were then centrifuged at 4° C., 10 min at 600 g. Supernatant was then centrifuged at 100 000 g for 25 min at 4° C. Pellet was rinsed with 150 µL of rinse buffer and centrifuged in the same conditions as above. The final pellet was resuspended with 150 µL of $NH_4HCO_3$ 50 mM and homogenized. Membranous proteins were analysed on SDS-PAGE gels (4% stacking and a 12% running gel) stained with a MS-compliant silver nitrate staining protocol. All proteins were excised in one large strip which was minced in 1 $mm^3$ cubes just before protein reduction, alkylation (DTT, Iodoacetamide) and trypsin digestion (500 ng in AMBIC 50 mM, ACN 5%). Finally, peptides were extracted with 20 µL of ACN 30% FA 0,1%. Mass spectrometry analysis was performed with 4 µL injections on an online LC-MS composed by a nanoHPLC Dionex Ultimate 3000 and a Thermofisher QExactive+ with a 2 h gradient. All the proteomic steps were done under the supervision of the proteomic facility from La Pitié-Salpétrière (P35, UPMC), the LC-MS analysis has been performed on the proteomic facility of Paris-Descartes university (3P5, Paris Descartes).

The software used was X!Tandem (Ver: 2015.04.01.1), using X!Tandem pipeline (Ver: 3.4.3) and the Uniprot reference proteome used was downloaded on Dec. 12, 2016. Standard contaminants were removed. Filter applied: Proteins with at least 1 peptide with e value <0.05; FDR peptide=0.128; FDR protein=0.95. Final protein score Log(e value)<−2. Final results gave 1679 groups with 1831 subgroups.

The protein list obtained from LC-MS analysis has been manually filtered to keep only plasma membrane proteins. This observed $PW1^+$ membranome has been confronted with the putative PW1+ membranome. Only proteins found in both lists were treated. Potential candidates were then selected according to literature and antibodies validated for flow cytometry & immunofluorescence staining availability.

Western Blot Analysis

Proteins from mouse heart were extracted from frozen tissues with Dounce-Potter homogenization into ice-cold RIPA buffer (50 mM Tris pH7.4, 150 mM NaCl, 1% Igepal CA-630, 50 mM deoxycholate, and 0.1% SDS) containing antiproteases (Sigma-Aldrich), serine/threonine and tyrosine protein phosphatase inhibitors (Phosphatase inhibitor Cocktail 2 and 3, Sigma-Aldrich) and 1 mM $Na_3VO_4$ or with urea-thiourea buffer (5 M urea, 2 M thiourea, 50 mM DTT, 0.1% [w/v] SDS in PBS pH 7.4). After 1 h incubation at 4° C., the homogenate was centrifuged at 15 300 g for 15 min at 4° C. and the supernatant containing proteins was collected. Protein concentrations for all samples were determined with a Bradford-based method protein assay (Biorad).

After sorting, the heart $PW1^+$ cells of 22 mice and the heart $PW1^-$ cells of 16 mice were pooled and centrifuged at 500 g for 15 min at 4° C. and lysed in urea-thiourea buffer. Proteins were extracted as describe above.

Cardiac myocytes (CM) and non-cardiomyocyte (non-CM) cells were isolated from the adult mouse heart as previously described with minor modifications (Ackers-Johnson et al, 2016). After cell collection, CM were lysed in RIPA and urea-thiourea buffer for protein extraction as describe above and non-CM where plated in growth medium (DMEM 10% FBS 1% P/S). Proteins were extracted in RIPA and urea-thiourea buffer when cells reached 80% confluence.

Proteins (10-30 µg) were mixed with NuPAGE™ LDS sample buffer, NuPAGE™ Sample Reducing Agent and extraction buffer, incubated at 70° C. for 10 min and then loaded onto a gel lane of a NuPAGE™ Novex® 4-12% Bis-Tris gel (Life Technologies). After 3 h running at 90 V with NuPAGE™ MES SDS running buffer (Life Technologies), proteins were transferred to nitrocellulose membranes and blocked for 1 h in Tris-buffered saline with 0.1% Tween-20 (TBS-Tween) containing 5% skim milk with constant shaking. Membranes were then incubated with primary antibodies specific for CD51 (Bioss), Integrin beta 1 (Abcam), Integrin beta 3 (Cell Signaling), Integrin beta 5 (Cell Signaling) and Integrin beta 8 (Sigma-Aldrich) diluted in 5% BSA/TBS-Tween overnight at 4° C. with constant shaking. Membranes were then washed with TBS-Tween and incubated for 1 h at room temperature (RT) with horseradish peroxidase labelled secondary antibodies diluted in 5% skim milk or BSA/TBS-Tween for 1 h. Membranes were then washed again with TBS-Tween and then incubated for 5 min SuperSignal™ West Pico PLUS Chemiluminescent Substrate (Life Tecnologies) before imaging with the Chemidoc® XRS+ camera (Biorad) and the Image Lab™ software.

Pharmacological Inhibition of $Pw1^+$ Cells In Vitro

FACS sorted $PW1^+$ or $PW1^-$ cells were plated at the density of 25 000 cell per $cm^2$ in culture plates coated with attachment factor (ThermoFisher Scientific). Cells were left to adhere overnight with 0.5 mL of growth medium (DMEM 10% FBS 1% P/S). The culture medium was changed the day after. At day 5, culture media was changed and supplemented with 0, 300 nM, or 1 µM of cilengitide. At day 6, medium was removed, and cells were washed twice with PBS. Cells were then lysed and RNA extracted followed by an RT-PCR. A Q-PCR was finally performed on selected fibrosis markers.

Statistical Analysis

The data of this manuscript were expressed as mean±SEM. When comparing more than 2 groups, quantitative data were analyzed using one-way ANOVA and pair wise comparisons with Tukey's test for multiple comparisons. The Mann Whitney U test was used for comparing continuous variables between 2 groups. A log rank (Mantel-Cox) test was used to compare survival between groups. P-values <0.05 were considered significant.

Results

Bioinformatic Analysis Defines Cardiac PW1+ Cells Putative Membranome

We first characterized the transcriptome profile of cardiac PW1+ cells by RNA-sequencing. For this purpose, cardiac PW1+ were FACS-isolated from fresh cardiac tissues using our PW1$^{nLacZ}$ reporter mouse model using $C_{12}FDG$, a fluorescent substrate for β-galactosidase activity. We obtained cardiac PW1+ from normal hearts as well as from ischemic hearts (i.e., seven days after MI). We then used filtered, aligned, quality-controlled RNA-seq output files to predict amino acid sequences of the corresponding genes and we then used a series of bioinformatics algorithms to identify putative membrane proteins (data not shown). Briefly, we considered proteins with a predicted N-terminal endoplasmic reticulum targeting signal peptide and predicted transmembrane domains but with no intracellular localization signals (i.e., no ER retention signal motif and no mitochondrial targeting peptide nor Nuclear export signal). By progressive filtering, we thus generated a list of 2040 candidate expressed in cardiac PW1+ cell membranes in both normal and ischemic conditions (data not shown). The characteristics of these 2040 candidates were further screened in available databases to identify 913 candidates as more likely expressed in the plasma membrane of cardiac PW1+ cells (data not shown). We then performed the same strategy to define the putative surface membranome of other cell types (i.e., cardiomyocytes, non-myocytes heart fractions and embryonic stem cells) and performed a last screen to limit our list to 378 candidates that were only observed in the datasets obtained in cardiac PW1+ cells (data not shown). Functional enrichment analysis of this short list of cardiac PW1+-specific and condition-insensitive cell surface markers identified an important number of transmembrane receptors, transporters, and a smaller proportion of ion channels and enzymes (data not shown). However, the molecular function was not described for the majority of the identified candidates.

Proteomic Analysis Cross-Validates the Expression of 9 Cell Surface Proteins in Cardiac PW1+ Cells In parallel of the transcriptomics approach, we also performed a proteomic analysis of FACS-isolated cardiac PW1+ cells using mass spectrometry (data not shown). We identified the expression of 1885 proteins which were further analyzed in available databases in order to restrict the dataset to 230 proteins with plasma membrane location. We then made a direct comparison of the transcriptomics and proteomics datasets and confirmed the cross-identification of 9 candidates with both approaches (data not shown). Among these 9 cell surface proteins, we found 3 transporters, 4 receptors and 2 enzymes and most of these candidates were involved in cell motility, adhesion to the matrix and response to wounding (data not shown). Five of these candidates were already described in non-cardiac cells as plasma membrane clusters of differentiation (i.e., CD51-Itgav, CD140a-Pdgfra, CD172a-Sirpa, CD39-Entpd1 and CD163) and were further considered for the remainder of our study.

Itgav (CD51) is Highly Expressed in Cardiac PW1+ Cells

The expression of these 5 newly identified cell surface markers was analyzed by cytometry in $C_{12}FDG^+$ cells isolated from PW1$^{nLacZ}$ reporter mouse hearts. We strikingly observed that 92.98±1.01% of cardiac PW1+ cells express CD51 (data not shown). The four other new markers as well as typical adult stem cell markers (i.e., CD44, CD34, CD166) were expressed in a lower proportion (i.e., around 50%) of cardiac PW1+ cells (data not shown), thus indicating CD51 as a potent marker to discriminate cardiac PW1+ cells. Further analyses in sorted CD45− Ter 19− cardiac cells showed the high clustering of FDG and CD51 expression, further confirming that resident cardiac PW1+ cells display a high expression level of CD51 (data not shown). Reciprocally, CD51 expression was observed in the majority of FDG+ CD45+ Ter 19− cardiac cells (data not shown).

In order to develop and validate a new sorting strategy for cardiac PW1+ cells based on CD51 expression, we first analyzed the expression of the four other studied candidates in CD51 sorted cells from PW1$^{nLacZ}$-reporter mice hearts and found that FDG+ CD51+ CD45− cells exclusively express CD140a (i.e, PDGF receptor alpha) while FDG+ CD51+ CD45+ cells express CD172a (data not shown). Using our PW1$^{nLacZ}$ reporter mouse, we then started cell selection using CD51, CD45, CD140a and CD172 in order to propose a new sorting strategy of cardiac PW1+ cells. Briefly, the cardiac CD51+ populations can be easily segregated according to CD45, CD140a and CD172 expression (data not shown). We then assessed beta-galactosidase activity in each of these sub-populations and found that the new strategy allows to recover 84.57±1.61% of PW1+ cells among the CD51+CD45− CD140a+CD172− population and 91.13±0.81% among the CD51+ CD45+ CD140a− CD172+ population. These results indicated CD51 as being expressed in almost all cardiac PW1+ cells, and as being predominantly found in cells expressing PW1+ in the myocardium.

Cardiac PW1+ Cells Express Different αV-Containing Integrins

CD51 (Itgav) belongs to the family of integrins that are transmembrane receptors which act as bridges for cell-ECM connections and cell-cell interactions. We thus first analyzed CD51 expression in cardiomyocytes and non-myocytes fractions freshly isolated from mouse normal hearts. Huvec cells were used as positive controls. We found that CD51 was exclusively expressed in the non-myocytes fractions (data not shown). We then FACS-sorted PW1+ and PW1− cell fractions from normal and ischemic mice hearts and found that CD51 expression was only observed in cardiac PW1+ cells (data not shown), thus further corroborating the transcriptomics, proteomics and cytometry data. Western blots analyses further confirmed a significant increase in CD51 expression in ischemic hearts and more specifically in the infarct zone (data not shown), which is consistent with a predominant expression in cardiac PW1+ cells as we previously showed a significant increase in the number of cardiac PW1+ cells post-MI with a predominant location to the infarct area[19].

Integrin alphaV subunits can combine to beta subunits to form different integrin combinations that can be more abundantly observed in some particular cell types. We thus sought for a peculiar integrin signature in cardiac PW1+ cells. We firstly assessed the expression of Itgav and beta subunits (including Itgb1, Itgb3, Itgb5, and Itgb8) using our transcriptomic data sets. In line with our western blot data, Itgav was predicted as more abundant in cardiac PW1+ cells than in other studied cell types. We then found that the mRNA expression level of Itgb1 was higher as compared to other integrin beta subunits in cardiac PW1+ cells as well as in other studied cell types (data not shown), suggesting a predominant αVβ1 complex in cardiac PW1+ cells. Western blotting in cardiac cell fractions (data not shown) confirmed the presence of ITGβ1 ITGβ3, ITGβ5, and ITGβ8 in non-myocytes cells. The presence of ITGβ1 but also of ITGβ3 was further confirmed in cardiac PW1+ cells while ITGβ5, and ITGβ8 were not observed in these cells (data not shown). Consistently, ITGβ1 and ITGβ3 were over-expressed in the infarct areas of post-MI hearts (data not shown). Overall, these results confirm the predominant expression of CD51 (i.e., ITGAV) in PW1+ cells in the myocardium and suggest the principal presence of αVβ1 and αVβ3 heterodimers in cardiac PW1+ cells.

Targeting PW1+αV Integrin Reduce Cardiac Fibrosis after MI

Recent evidence have shown αV integrins as central mediators of organ fibrosis through TGF-beta activation[22,23] with a key role of αVβ1 integrin among others. Our results showed that CD51 can be used as a cell surface marker to identify PW1+ cells but we then wondered whether CD51 can also directly participate in the cardiac PW1+ fibrogenic behavior as previously described[19]. CD51 (αV integrin) recognizes and binds the tripeptide sequence RGD (arginine, glycine, aspartic acid) which is a key motif for cell-cell and cell-ECM interactions. Based on this motif, a cyclic RGD pentapeptide was developed (called cilengitide) and was shown to exert strong inhibiting activity against the integrin αV, including αVβ1, αVβ3 and αVβ5.

Figure 1A:
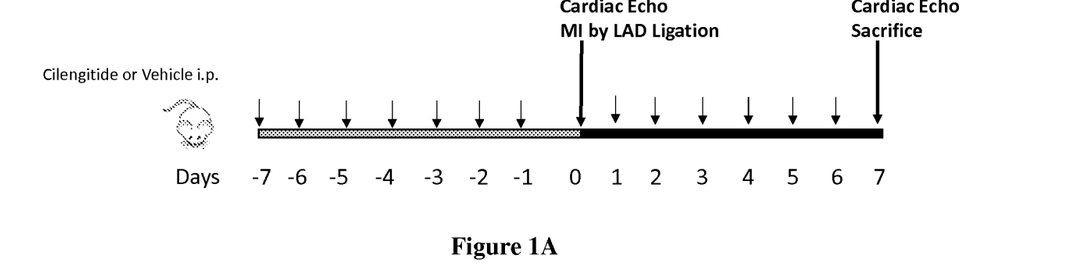
Figure 1B:
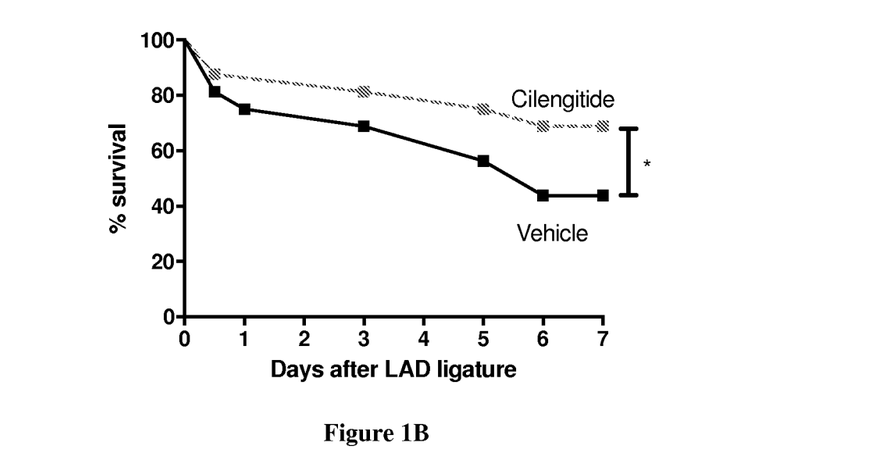
Figure 1C:
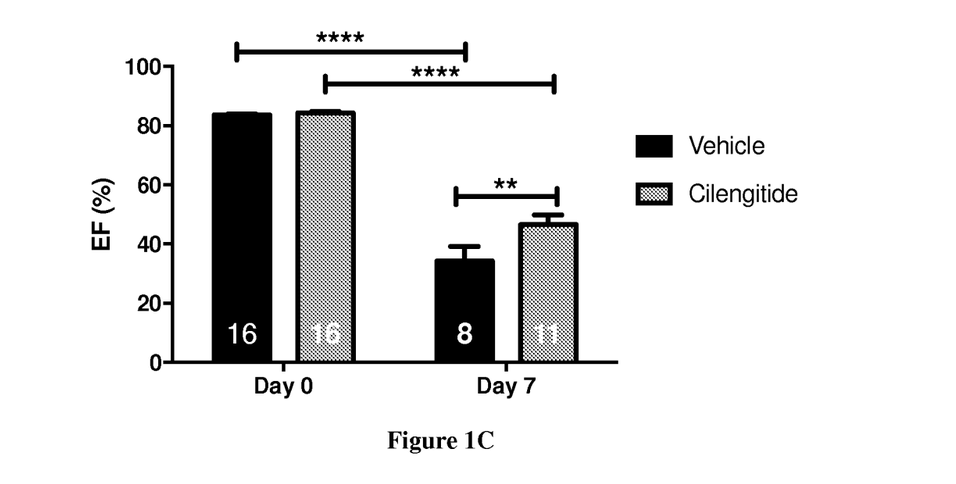
Figure 1D:
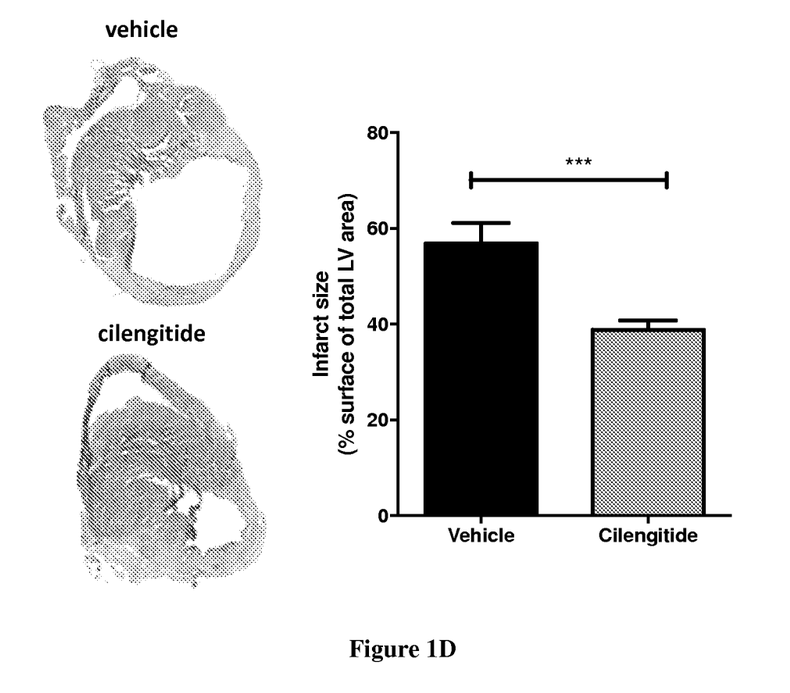
Figure 1E:
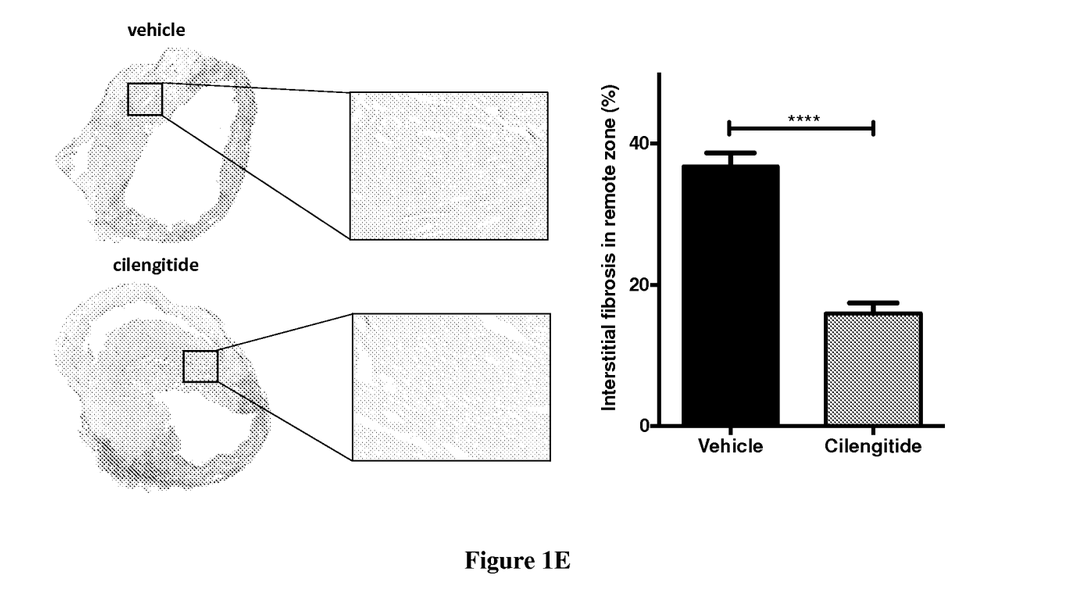

To further assess the potential contribution of αV integrin as found in cardiac PW1+ cells, we examined the potential of αV integrins pharmacological blockade to prevent cardiac fibrosis in response to an ischemic injury. Mice were pre-treated for 7 days with cilengitide or vehicle and were then subjected to MI via a complete LAD ligation. The mice were further daily treated with cilengitide or vehicle for additional 7 days before final evaluation of cardiac function and remodeling (FIG. 1a). We found that cilengitide treatment was associated 7 days after MI with a significant improvement in survival (FIG. 1b) that correlated with a significant increase in cardiac function as measured by left ventricular ejection fraction (FIG. 1c). Collagen (masson trichrome and picrosirius red) stainings were then performed on 8 sequential cardiac sections (data not shown). Digital image quantification demonstrated a significant reduction in infarct size (38.8±7.9% vs. 56.8±14.9% in cilengitide vs. vehicle respectively, p=0.0008, FIG. 1d) as well as in interstitial fibrosis measured in the remote myocardial area (15.9±10.4% vs. 36.8±13.1% in cilengitide vs. vehicle respectively, p<0.0001, FIG. 1e), while cilengitide treatment was not associated with any changes in survival, cardiac function or cardiac fibrosis in sham animals (data not shown).

αV Integrin Blockade Reduces the Fibrogenic Behavior or Cardiac PW1+ Cells

Figure 2A:
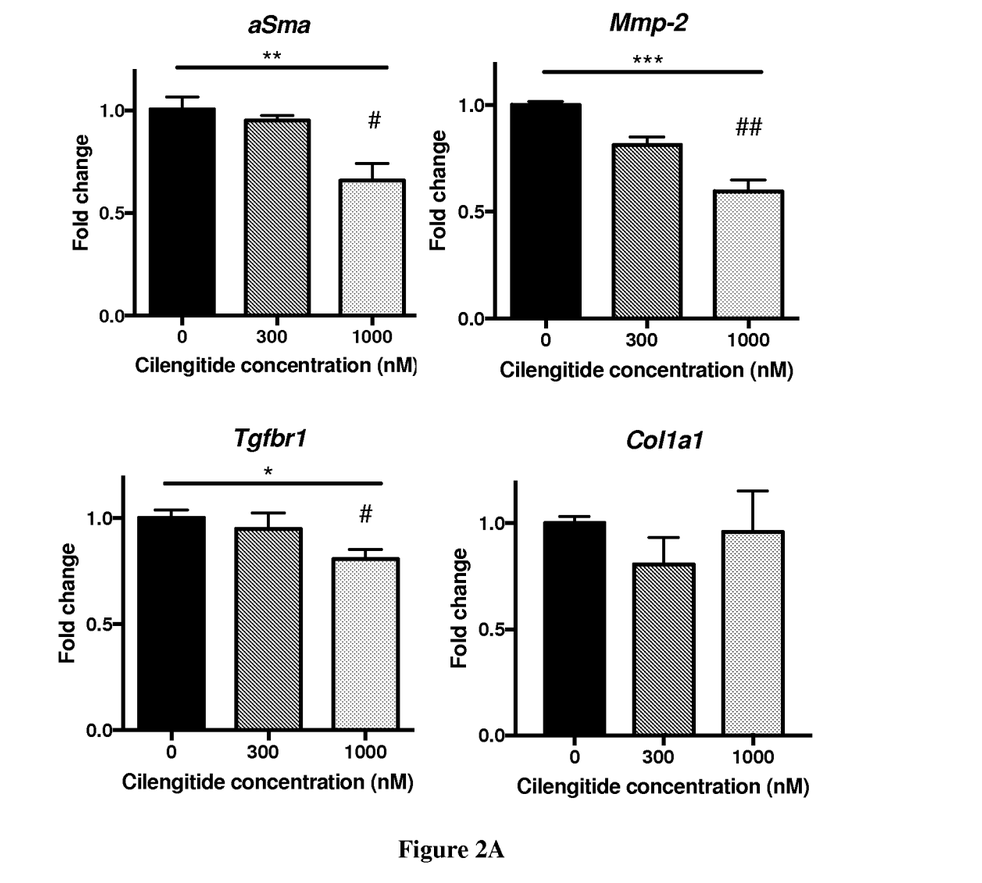

Overall, these results suggest a primary blunting of mechanisms leading to the development of cardiac fibrosis in response to MI, a phenomenon that could involve cardiac PW1+ cells as they were previously shown to display a fibrogenic behavior post-MI[19] and we here showed that they predominantly express αV integrins which are targeted by cilengitide. To test this hypothesis, we first investigated whether CD51 pharmacological inhibition affects the expression of profibrotic genes in freshly FACS-isolated cardiac PW1+ cells. These cells were seeded and cultured for 4 days and then treated for 48 h with growing concentrations of cilengitide or vehicle. Cilengitide treatment resulted in significant down-regulation of aSma (or Acta2), mmp2 and tgfrb1 (FIG. 2a), suggesting a reduction in TGF-beta signaling and myofibroblast differentiation capacity. Col1a1 expression was however not affected by cilengitide treatment, supporting a specific regulatory role on individual ECM genes.

Figure 2B:
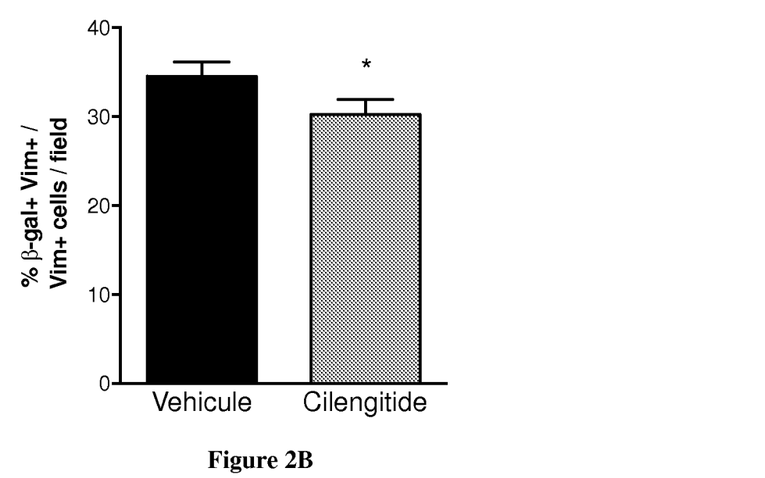
Figure 2C:
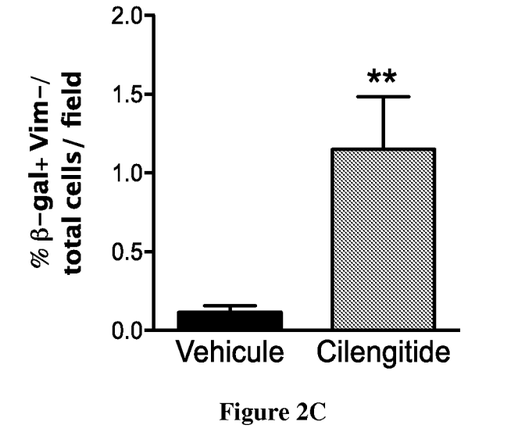

We then performed short-term lineage tracing of cardiac PW1+ cells using PW1$^{nLacz}$-reporter mouse model. The stability (produrance) of the β-gal reporter indeed allows for identification of cells derived from β-gal+ cells. We examined β-gal activity and a typical fibroblast marker (i.e., vimentin) expression in vivo in cardiac sections of post-MI (7 days) hearts and found that cilengitide treatment was associated with a significant reduction in the proportion of cells co-expressing β-gal and vimentin (FIG. 2b). Reciprocally, we found a significant increase in the number of β-gal+ cells that did not express vimentin after cilengitide treatment (FIG. 2c). Overall, these results suggest that αV integrin blockade with cilengitide impacted the ability of cardiac PW1+ cells to differentiate into fibroblast and contribute to fibrotic scarring.

Discussion:

To the best of our knowledge, we provide here the first description of proteins expressed at the cell surface of PW1+ cardiac adult stem cells. The identification of a cell-surface markers signature is critical for the isolation, characterization and understanding of resident adult stem cells as these cells typically represent a small proportion of the living cells in an organ. In addition, there is a diversity of markers that have been proposed but with a significant overlap between markers and a limited discriminatory power. For instance, we here found that typical stem cells markers (e.g., CD140a, CD44, CD166) are indeed found at the surface of cardiac PW1+ cells but in only ~50% of these cells. So far, the identification of PW1+ cells has been made possible through the use of a transgenic PW1-reporter mouse model that revealed extremely potent to demonstrate PW1 as a pan-tissue stem cell marker[19,20,27-29]. We here used this model to specifically isolate cardiac PW1+ cells and then performed a multi-omics unbiased approach to further decipher the cell-surface membranome of these cells. The transcriptomics predictions helped us to strikingly filter down the large number of membrane proteins identified through a mass spectrometry technique and therefore increased the likelihood to identify a more specific cell surface marker among the limited number of remaining candidates. A similar approach was recently proposed to define the secretome of bone marrow stem cells[30].

We then found CD51 as being expressed in the very large majority of cardiac PW1+ cells, a result that was not previously reported nor anticipated. Reciprocally, CD51 is predominantly found in cells expressing PW1+ in the myocardium thus highlighting the discriminative value of this new marker that could now serve for PW1+ cells sorting. Whether CD51 specifically tags PW1+ cells in non-cardiac organs however remains to be determined.

The identification of this new cell surface marker then provided important information on the pathophysiological role of cardiac PW1+ cells. CD51 is an αV-integrin subunit, a subset of integrin family cell adhesion receptors that were recently suggested as central mediators of organ fibrosis through TGF-beta activation[22,23]. Strikingly, we recently reported that cardiac PW1+ cells display a fibrogenic behavior in response to ischemic injury, notably by directly giving rise to fibroblasts[19]. Our new results indicate that CD51 (or ITGAV) play a direct role in controlling the fibrogenic fate of cardiac PW1+ cells. We indeed found that blockade of αV-integrin limits the expression of fibrotic genes in isolated cardiac PW1+ cells and reduce the ability of cardiac PW1+ cells to differentiate into fibroblasts in vivo in in a MI murine model. Pharmacological blockade of αV-integrin with cilengitide in this model significantly reduced the post-MI fibrotic remodeling, with a significant reduction in infarct size and interstitial fibrosis. The survival and cardiac function of cilengitide treated animals were consequently improved. As some integrins are expressed in endothelial cells, it has been suggested that cilengitide has some anti-angiogenic effects[31]. However, this mechanism could not explain our current observations as an anti-angiogenic effect should have adversely deteriorated cardiac function post-MI. Similarly, ITGβ3 can be expressed by endothelial cells but we found a significant increase in ITGβ3 expression in the infarct area, a zone typically depleted in vessels but enriched with PW1+ cells. Our data rather show that αV-integrins are predominantly expressed in PW1+ cells within the cardiac cells, thus suggesting that the observed benefit on cardiac fibrotic remodeling is primarily carried out by reducing the fibrogenic behavior of these cells. A contribution of circulating cells (such as inflammatory cells in response to cardiomyocyte necrosis) can however not be ruled out.

The role of integrins in non-cardiac organ fibrosis (i.e., lung and liver) is becoming increasingly recognized and genetic deletion or pharmacological inhibition of integrins have been associated with reduced fibrotic remodeling[23,32,33]. Interestingly, these recent studies indicate a critical role of αVβ1 in organ fibrosis[23,32]. The role of αVβ1 heterodimers as well as mesenchymal-like cells αV integrins in the development of muscular and cardiac fibrosis have only been recently acknowledged[23,34]. Our present data further provide evidence for a role of cardiac PW1+ adult stem cells in the development of cardiac fibrosis through αV integrins. Our results are compatible with the hypothesis that cardiac PW1+ cells represent a cellular source of fibrosis by directly differentiating into fibroblasts. It is however also possible that cardiac PW1+ cells indirectly contribute to fibrosis by orchestrating a microenvironment that further favors the activation of resident fibroblasts or the remodeling of the extracellular matrix. Our data suggest some specific changes in individual ECM genes (notably related to TGF-beta pathway) after αV-integrin blockade, an observation that will deserve further experiments.

Lastly, our study indicates that a new anti-fibrotic therapy could be developed by targeting αV-integrins as expressed in the fibrogenic cardiac PW1+ cells. So far, heart failure therapies are used to alleviate cardiac workload and indirectly reduce cardiac remodeling but there is currently no effective anti-fibrotic therapeutic strategy that could complement the current therapies for HF[9,11,12] To achieve an antifibrotic therapy, a better understanding of the mechanisms contributing to cardiac fibrosis is needed and our data report on a new cellular source of cardiac fibrosis. Importantly, in our study, pharmacological blockade of αV-integrin was associated with favorable outcomes in a murine MI model. Anti-fibrotic strategies in MI often exposed to the risk of cardiac rupture by limiting the development of replacement fibrosis which restores the region devoid of viable cardiomyocytes and prevents cardiac rupture[35]. For instance, it was recently shown that strategies that limits inflammatory cells recruitment to the site of infarction delayed the removal of dead cardiomyocytes and their replacement by a scar tissue, therefore increasing susceptibility to cardiac rupture[36]. We did not observe such an adverse outcome but rather found a significant improvement in survival under cilengitide treatment. Combined with the significant reduction in interstitial fibrosis in cilentigitide treated animals, this suggests that blockade of αV-integrin does not directly affect the replacement fibrotic remodeling but rather limits the development of reactive interstitial fibrosis in the viable myocardium[12].

Overall, these data identify cardiac PW1+ cells as a source of cardiac fibrosis in response to an ischemic injury via αV-integrin and suggest that pharmacological targeting of αV-integrin may provide clinical benefit in the treatment of cardiac ischemia.

REFERENCES

Throughout this application, various references describe the state of the art to which this invention pertains. The disclosures of these references are hereby incorporated by reference into the present disclosure.

1. Maggioni, A. P., et al. EURObservational Research Programme: regional differences and 1-year follow-up results of the Heart Failure Pilot Survey (ESC-HF Pilot). Eur J Heart Fail 15, 808-817 (2013).
2. Roger, V. L., et al. Heart disease and stroke statistics—2012 update: a report from the American Heart Association. Circulation 125, e2-e220 (2012).
3. Seferovic, P. M., et al. Organization of heart failure management in European Society of Cardiology member countries: survey of the Heart Failure Association of the European Society of Cardiology in collaboration with the Heart Failure National Societies/Working Groups. Eur J Heart Fail 15, 947-959 (2013).
4. Ponikowski, P., et al. 2016 ESC Guidelines for the diagnosis and treatment of acute and chronic heart failure: The Task Force for the diagnosis and treatment of acute and chronic heart failure of the European Society of Cardiology (ESC)Developed with the special contribution of the Heart Failure Association (HFA) of the ESC. Eur Heart J 37, 2129-2200 (2016).
5. Savarese, G. & Lund, L. H. Global Public Health Burden of Heart Failure. Card Fail Rev 3, 7-11 (2017).
6. Dunlay, S. M., Roger, V. L. & Redfield, M. M. Epidemiology of heart failure with preserved ejection fraction. Nat Rev Cardiol 14, 591-602 (2017).
7. Lewis, G. A., et al. Biological Phenotypes of Heart Failure With Preserved Ejection Fraction. J Am Coll Cardiol 70, 2186-2200 (2017).
8. Gyongyosi, M., et al. Myocardial fibrosis: biomedical research from bench to bedside. Eur J Heart Fail 19, 177-191 (2017).
9. Schelbert, E. B., Fonarow, G. C., Bonow, R. O., Butler, J. & Gheorghiade, M.

Therapeutic targets in heart failure: refocusing on the myocardial interstitium. J Am Coll Cardiol 63, 2188-2198 (2014).
10. Li, A. H., Liu, P. P., Villarreal, F. J. & Garcia, R. A. Dynamic changes in myocardial matrix and relevance to disease: translational perspectives. Circ Res 114, 916-927 (2014).
11. Gourdie, R. G., Dimmeler, S. & Kohl, P. Novel therapeutic strategies targeting fibroblasts and fibrosis in heart disease. Nat Rev Drug Discov 15, 620-638 (2016).
12. Travers, J. G., Kamal, F. A., Robbins, J., Yutzey, K. E. & Blaxall, B. C. Cardiac Fibrosis: The Fibroblast Awakens. Circ Res 118, 1021-1040 (2016).
13. Kramann, R., et al. Perivascular Gli1+ progenitors are key contributors to injury-induced organ fibrosis. Cell Stem Cell 16, 51-66 (2015).
14. Kalluri, R. The biology and function of fibroblasts in cancer. Nat Rev Cancer 16, 582-598 (2016).

15. Teekakirikul, P., et al. Cardiac fibrosis in mice with hypertrophic cardiomyopathy is mediated by non-myocyte proliferation and requires Tgf-beta. J Clin Invest 120, 3520-3529 (2010).
16. Olivey, H. E., Mundell, N. A., Austin, A. F. & Barnett, J. V. Transforming growth factor-beta stimulates epithelial-mesenchymal transformation in the proepicardium. Dev Dyn 235, 50-59 (2006).
17. Duan, J., et al. Wntl/betacatenin injury response activates the epicardium and cardiac fibroblasts to promote cardiac repair. EMBO J 31, 429-442 (2012).
18. Humphreys, B. D., et al. Fate tracing reveals the pericyte and not epithelial origin of myofibroblasts in kidney fibrosis. Am J Pathol 176, 85-97 (2010).
19. Yaniz-Galende, E., et al. Fibrogenic Potential of PW1/Peg3 Expressing Cardiac Stem Cells. J Am Coll Cardiol 70, 728-741 (2017).
20. Besson, V., et al. PW1 gene/paternally expressed gene 3 (PW1/Peg3) identifies multiple adult stem and progenitor cell populations. Proc Natl Acad Sci USA 108, 11470-11475 (2011).
21. Mitchell, K. J., et al. Identification and characterization of a non-satellite cell muscle resident progenitor during postnatal development. Nat Cell Biol 12, 257-266 (2010).
22. Henderson, N. C., et al. Targeting of alphav integrin identifies a core molecular pathway that regulates fibrosis in several organs. Nat Med 19, 1617-1624 (2013).
23. Chen, C., Li, R., Ross, R. S. & Manso, A. M. Integrins and integrin-related proteins in cardiac fibrosis. J Mol Cell Cardiol 93, 162-174 (2016).
24. Chen, C., Khaleel, S. S., Huang, H. & Wu, C. H. Software for pre-processing Illumina next-generation sequencing short read sequences. Source Code Biol Med 9, 8 (2014).
25. Li, B. & Dewey, C. N. RSEM: accurate transcript quantification from RNA-Seq data with or without a reference genome. BMC Bioinformatics 12, 323 (2011).
26. Yates, A., et al. Ensembl 2016. Nucleic Acids Res 44, D710-716 (2016).
27. Dierick, F., et al. Resident PW1+ Progenitor Cells Participate in Vascular Remodeling During Pulmonary Arterial Hypertension. Circ Res 118, 822-833 (2016).
28. Sojoodi, M., et al. The zinc finger transcription factor PW1/PEG3 restrains murine beta cell cycling. Diabetologia 59, 1474-1479 (2016).
29. Besson, V., et al. Expression Analysis of the Stem Cell Marker Pw1/Peg3 Reveals a CD34 Negative Progenitor Population in the Hair Follicle. Stem Cells 35, 1015-1027 (2017).
30. Korf-Klingebiel, M., et al. Myeloid-derived growth factor (C19orf10) mediates cardiac repair following myocardial infarction. Nat Med 21, 140-149 (2015).
31. Nisato, R. E., Tille, J. C., Jonczyk, A., Goodman, S. L. & Pepper, M. S. alphav beta 3 and alphav beta 5 integrin antagonists inhibit angiogenesis in vitro. Angiogenesis 6, 105-119 (2003).
32. Reed, N. I., et al. The alphavbeta1 integrin plays a critical in vivo role in tissue fibrosis. Sci Transl Med 7, 288ra279 (2015).
33. Conroy, K. P., Kitto, L. J. & Henderson, N. C. alphav integrins: key regulators of tissue fibrosis. Cell Tissue Res 365, 511-519 (2016).
34. Murray, I. R., et al. alphav integrins on mesenchymal cells regulate skeletal and cardiac muscle fibrosis. Nat Commun 8, 1118 (2017).
35. Sun, Y. & Weber, K. T. Infarct scar: a dynamic tissue. Cardiovasc Res 46, 250-256 (2000).
36. Lorchner, H., et al. Myocardial healing requires Reg3beta-dependent accumulation of macrophages in the ischemic heart. Nat Med 21, 353-362 (2015).

The invention claimed is:

1. A method of ameliorating cardiac fibrosis in a patient in need thereof comprising administering to the patient a therapeutically effective amount of a single αV-integrin inhibitor, wherein the αV-integrin inhibitor is cilengitide, and wherein the cardiac fibrosis occurs in response to myocardial infarction.

2. The method of claim 1 wherein the αV-integrin inhibitor limits the development of reactive interstitial fibrosis in the viable myocardium.

3. The method of claim 1 wherein the αV-integrin inhibitor improves cardiac function.

4. A method of ameliorating cardiac fibrosis in a patient suffering from acute myocardial infarction, comprising administering to the patient a therapeutically effective amount of cilengitide, wherein administration of the cilengitide reduces differentiation of PW1+ cardiac adult stem cells into fibroblasts and limits the development of reactive interstitial fibrosis.

5. The method of claim 4, wherein administration of the cilengitide reduces infarct size and/or attenuates extension of reactive cardiac fibrosis.

6. The method of claim 4, wherein administration of the cilengitide improves cardiac function after acute myocardial infarction.

7. The method of claim 4, wherein administration of cilengitide improves survival as compared to a patient suffering from acute myocardial infarction and not administered cilengitide.

* * * * *